US010966786B2

(12) United States Patent
Ludwin et al.

(10) Patent No.: US 10,966,786 B2
(45) Date of Patent: Apr. 6, 2021

(54) REAL-TIME ESTIMATION OF TISSUE PERFORATION RISK DURING MINIMALLY INVASIVE MEDICAL PROCEDURE

(71) Applicant: BIOSENSE WEBSTER (ISRAEL) LTD., Yokneam (IL)

(72) Inventors: Doron Moshe Ludwin, Haifa (IL); Eitan Peri, Givat Ada (IL); Eyal Yechezkel Glottmann, Haifa (IL); Yevgeny Bonyak, Haifa (IL); Aharon Turgeman, Zichron Ya'acov (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 807 days.

(21) Appl. No.: 15/662,120

(22) Filed: Jul. 27, 2017

(65) Prior Publication Data

US 2017/0325893 A1    Nov. 16, 2017

Related U.S. Application Data

(62) Division of application No. 14/058,312, filed on Oct. 21, 2013, now Pat. No. 9,743,991.

(51) Int. Cl.
*A61B 34/10* (2016.01)
*A61B 5/00* (2006.01)
(Continued)

(52) U.S. Cl.
CPC ............ *A61B 34/10* (2016.02); *A61B 5/6885* (2013.01); *A61B 18/1492* (2013.01); *A61B 90/03* (2016.02); *A61B 5/7239* (2013.01); *A61B 2017/00022* (2013.01); *A61B 2017/00075* (2013.01); *A61B 2017/00115* (2013.01); *A61B 2017/00119* (2013.01); *A61B 2017/00128* (2013.01); *A61B 2018/00351* (2013.01);
(Continued)

(58) Field of Classification Search
CPC ............................ A61B 34/10; A61B 18/1492
See application file for complete search history.

(56) References Cited

U.S. PATENT DOCUMENTS

| 5,391,199 A | 2/1995 | Ben-Haim |
| 5,944,022 A | 8/1999 | Nardella et al. |

(Continued)

FOREIGN PATENT DOCUMENTS

| EP | 1229829 B1 | 9/2008 |
| EP | 2248480 A1 | 11/2010 |

(Continued)

OTHER PUBLICATIONS

European Search Report for corresponding application serial No. EP14189511, completed Feb. 25, 2015.
(Continued)

*Primary Examiner* — Daniel L Cerioni
*Assistant Examiner* — Yasmeen S Warsi (57) ABSTRACT

A method for performing a medical procedure, includes coupling a tip of a probe to tissue in an organ of a patient in order to apply the medical procedure using the probe. A force exerted by the tip on the tissue and a displacement of the tip created by the force are measured. A dependence of the force on the displacement is calculated. Based on the calculated dependence, a risk level of perforation of the tissue is estimated.

19 Claims, 3 Drawing Sheets

(51) Int. Cl.
*A61B 18/14* (2006.01)
*A61B 90/00* (2016.01)
A61B 17/00 (2006.01)
A61B 18/00 (2006.01)

(52) U.S. Cl.
CPC .............. *A61B 2018/00577* (2013.01); *A61B 2018/00898* (2013.01); *A61B 2090/065* (2016.02); *A61B 2562/02* (2013.01); *A61B 2562/0223* (2013.01)

(56) References Cited

U.S. PATENT DOCUMENTS

| | | | |
|---|---|---|---|
| 5,983,126 | A | 11/1999 | Wittkampf |
| 6,239,724 | B1 | 5/2001 | Doron et al. |
| 6,332,089 | B1 | 12/2001 | Acker et al. |
| 6,351,667 | B1 | 2/2002 | Godie |
| 6,456,864 | B1 | 9/2002 | Swanson et al. |
| 6,484,118 | B1 | 11/2002 | Govari |
| 6,618,612 | B1 | 9/2003 | Acker |
| 6,690,963 | B2 | 2/2004 | Ben-Haim et al. |
| 8,523,787 | B2 | 9/2013 | Ludwin et al. |
| 2002/0065455 | A1 | 5/2002 | Ben-Haim et al. |
| 2003/0120150 | A1 | 6/2003 | Govari |
| 2004/0068178 | A1 | 4/2004 | Govari |
| 2009/0093806 | A1 | 4/2009 | Govari et al. |
| 2009/0138007 | A1 | 5/2009 | Govari et al. |
| 2011/0282217 | A1 | 11/2011 | Nashef |
| 2012/0191181 | A1 | 7/2012 | Kassab et al. |
| 2012/0265102 | A1 | 10/2012 | Leo et al. |
| 2012/0310116 | A1* | 12/2012 | Ludwin .................. A61B 90/03 600/587 |
| 2014/0142438 | A1 | 5/2014 | Ludwin et al. |

FOREIGN PATENT DOCUMENTS

| | | |
|---|---|---|
| EP | 2529667 A2 | 12/2012 |
| WO | 9605768 A1 | 2/1996 |
| WO | 2008/115745 A2 | 9/2008 |

OTHER PUBLICATIONS

U.S. Appl. No. 13/152,423, filed Jun. 3, 2011, now U.S. Pat. No. 8,523,767.

U.S. Appl. No. 13/680,496, filed Feb. 26, 2013, now US Publication No. 2014/0142438.

* cited by examiner

REAL-TIME ESTIMATION OF TISSUE PERFORATION RISK DURING MINIMALLY INVASIVE MEDICAL PROCEDURE

CROSS REFERENCE TO RELATED APPLICATION

This is a divisional of application Ser. No. 14/058,312, filed Oct. 21, 2013, which is incorporated herein by reference.

FIELD OF THE INVENTION

The present invention relates generally to invasive medical procedures, and particularly to methods and systems for estimating the risk of tissue perforation during application of medical procedures.

BACKGROUND OF THE INVENTION

Minimally-invasive intracardiac ablation is the treatment of choice for various types of arrhythmias. To perform such treatment, the physician typically inserts a catheter through the vascular system into the heart, brings the distal end of the catheter into contact with myocardial tissue in areas of abnormal electrical activity, and then energizes one or more electrodes at or near the distal end in order to create tissue necrosis.

A number of systems for probe-based medical procedures, such as, for example, intracardiac ablation therapy, are commercially available, such as the CARTO™ system offered by Biosense Webster Inc. (Diamond Bar, Calif.). CARTO tracks the position and operating parameters of the distal end of the catheter and displays this information electronically on a three-dimensional (3D) anatomical map of the heart. CARTO enables the system operator to electronically tag locations that have been ablated on the map and thus to keep track of the progress of the procedure.

To apply a catheter-based procedure, the physician typically forces the catheter towards the heart inner surface tissue (myocardium). If during the medical procedure (e.g., ablation) the catheter exerts a force upon the tissue that is higher than the force the tissue can tolerate, the catheter may eventually perforate the tissue. As a result, blood or other fluids filling the heart chamber may flow through the perforated tissue to fill up the space between the heart and the pericardium (i.e., the pericardial cavity), a situation referred to as cardiac tamponade.

U.S. Pat. No. 6,351,667, whose disclosure is incorporated herein by reference, describes an apparatus for detecting pericardial effusion that includes a measurement apparatus connected to a wire probe to be anchored on the right heart ventricle and to two other wire probes to be anchored in different regions of the pericardial sac. The measurement apparatus measures and displays the change in impedance between the individual wire probes.

European Patent Application Publication EP 2248480, whose disclosure is incorporated herein by reference, describes various embodiments that predict the volume, area and/or depth of lesions created through the use of a force-time integration technique. Other embodiments control the energy delivered to the ablation probe based on the contact force between the ablation probe and the target tissue to prevent steam popping. In another aspect, various embodiments of the invention reliably visualize the predicted volume, area and/or depth of lesions created during ablation procedures. One embodiment visualizes the predicted lesions created utilizing a force contact density mapping procedure. Another embodiment visualizes the predicted lesions through the use of a force-time integration technique. Yet another embodiment visualizes the predicted lesions through the use of a force time and power (and/or current) integration technique. Other embodiments predict the occurrence and locations tissue damage such as perforation that occurred during the ablation process. Still other embodiments predict the occurrence and location of isolation gaps that may occur during or after the procedure.

European Patent EP 1229829, whose disclosure is incorporated herein by reference, describes a system for detecting the presence of a perforation in a body cavity. The system includes a fluid pressure source; a medical device insertable into a body cavity, the medical device fluidly coupled to the fluid pressure source for delivery of fluid to the body cavity; and a pressure sensor positioned to detect a pressure of the fluid delivered to the body cavity.

SUMMARY OF THE INVENTION

An embodiment of the present invention that is described herein provides a method for performing a medical procedure, including coupling a tip of a probe to tissue in an organ of a patient in order to apply the medical procedure using the probe. A force exerted by the tip on the tissue and a displacement of the tip created by the force are measured. A dependence of the force on the displacement is calculated. Based on the calculated dependence, a risk level of perforation of the tissue is estimated.

In some embodiments, calculating the dependence includes calculating a gradient of the force as a function of the displacement, and estimating the risk level includes comparing the gradient to a predefined gradient threshold. In other embodiments, estimating the risk level includes predicting that the perforation is not imminent upon detecting that the gradient is lower than the predefined gradient threshold. In yet other embodiments, estimating the risk level includes predicting that the perforation is imminent upon detecting that the gradient is higher than the predefined gradient threshold.

In an embodiment, estimating the risk level includes identifying that the perforation has occurred upon detecting that the force is inversely-related to the displacement. In another embodiment, measuring the displacement includes measuring a first position when the tip is initially coupled to the tissue, measuring a second position when the tip exerts the force on the tissue, and calculating the displacement as the difference between the second and the first positions. In yet another embodiment, the method further includes indicating the estimated risk level to an operator of the medical procedure.

In some embodiments, indicating the risk level includes indicating an audible or visual alert. In other embodiments, indicating the risk level includes outputting a first indication if the risk level indicates an imminent perforation, and outputting a second indication, different from the first indication, if the risk level indicates an actual perforation.

There is additionally provided, in accordance with an embodiment of the present invention, apparatus for performing a medical procedure. The apparatus includes an invasive probe and a processor. The invasive probe comprises a probe tip, which is configured to be coupled to tissue in an organ of a patient. The processor is coupled to the probe and is configured to measure a force exerted by the tip on the tissue and a displacement of the tip created by the force, to calculate a dependence of the force on the displacement, and to estimate, based on the calculated dependence, a risk level of perforation of the tissue.

There is additionally provided, in accordance with an embodiment of the present invention, a computer software product, including a non-transitory computer-readable medium in which program instructions are stored, which instructions, when read by a processor that is coupled to a tip of an invasive probe for applying a medical procedure to tissue in an organ to which the tip is coupled, cause the processor to measure a force exerted by the tip on the tissue and a displacement of the tip created by the force, to calculate a dependence of the force on the displacement, and to estimate, based on the calculated dependence, a risk level of perforation of the tissue.

The present invention will be more fully understood from the following detailed description of the embodiments thereof, taken together with the drawings in which:

DETAILED DESCRIPTION OF EMBODIMENTS

Overview

In minimally invasive procedures, the physician typically inserts a catheter through the vascular system into a body organ, and brings the distal end of the catheter into contact with the internal tissue surface of the organ. In some cases, such as cardiac ablation, the medical procedure requires that the catheter would exert a certain level of force or pressure on the tissue.

When the force exerted by the catheter is relatively small, tissue neighboring the catheter contact point is pushed away, forming a tent-like shape. This effect is referred to as tenting. In tenting, the tissue maintains flexibility and can safely tolerate the catheter force. At higher force levels, there is risk of tissue perforation that should be avoided.

Tissue perforation is of particular significance in medical procedures that cause the tissue under treatment to weaken. For example, during cardiac ablation, energy is applied to the tissue to create local necrosis. As a result, the structure or texture of the ablated tissue may change and/or the tissue may become thinner or weaker, and therefore the ablated tissue may not be able to tolerate the catheter force. In such medical procedures, there is a high risk of tissue perforation and accompanying complications.

Embodiments of the present invention that are described herein provide improved methods and systems for estimating the risk of tissue perforation during minimally invasive medical procedures. In an example embodiment, the catheter comprises sensors for performing real-time measurements of the catheter position (or displacement relative to some initial position) and of the force the catheter exerts upon the tissue. Force and displacement measurements are delivered to a processor that calculates from successive measurements differential changes (e.g., $\Delta F$ and $\Delta D$) to derive instantaneous gradient values $\Delta F/\Delta D$.

The magnitude and sign of the gradient are used for estimating the risk of tissue perforation. Experimentation has shown that as the catheter is pushed deeper into the tissue, the resistance of the tissue increases, and as a result a higher increase in the exerted force is required to achieve a constant increase in the displacement. In other words, the force-displacement gradient increases at higher force and displacement levels. Entry into a risk zone, in which perforation is imminent, corresponds to a force-displacement dependence that indicates a gradient that is higher than a predefined threshold. If the dependence changes sign, i.e., the force begins to decrease as a function of the displacement, perforation is likely to have occurred.

Thus, as long as the gradient is maintained positive and below a predefined risk threshold, the risk of imminent perforation is estimated to be low. If the processor detects positive gradient values above the risk threshold, the risk of perforation is estimated to be high. Moreover, a situation in which gradient values become negative is indicative of a high risk that actual perforation has occurred.

In some embodiments, the force and displacement measurements may be used, in addition to or instead of the force-displacement gradient, for estimating the risk of tissue perforation.

In various embodiments, the processor produces suitable alerts to the physician. Alerted by such real-time risk indications, the physician can take suitable measures, in advance, to predict and prevent tissue perforation.

System Description

Figure 1:
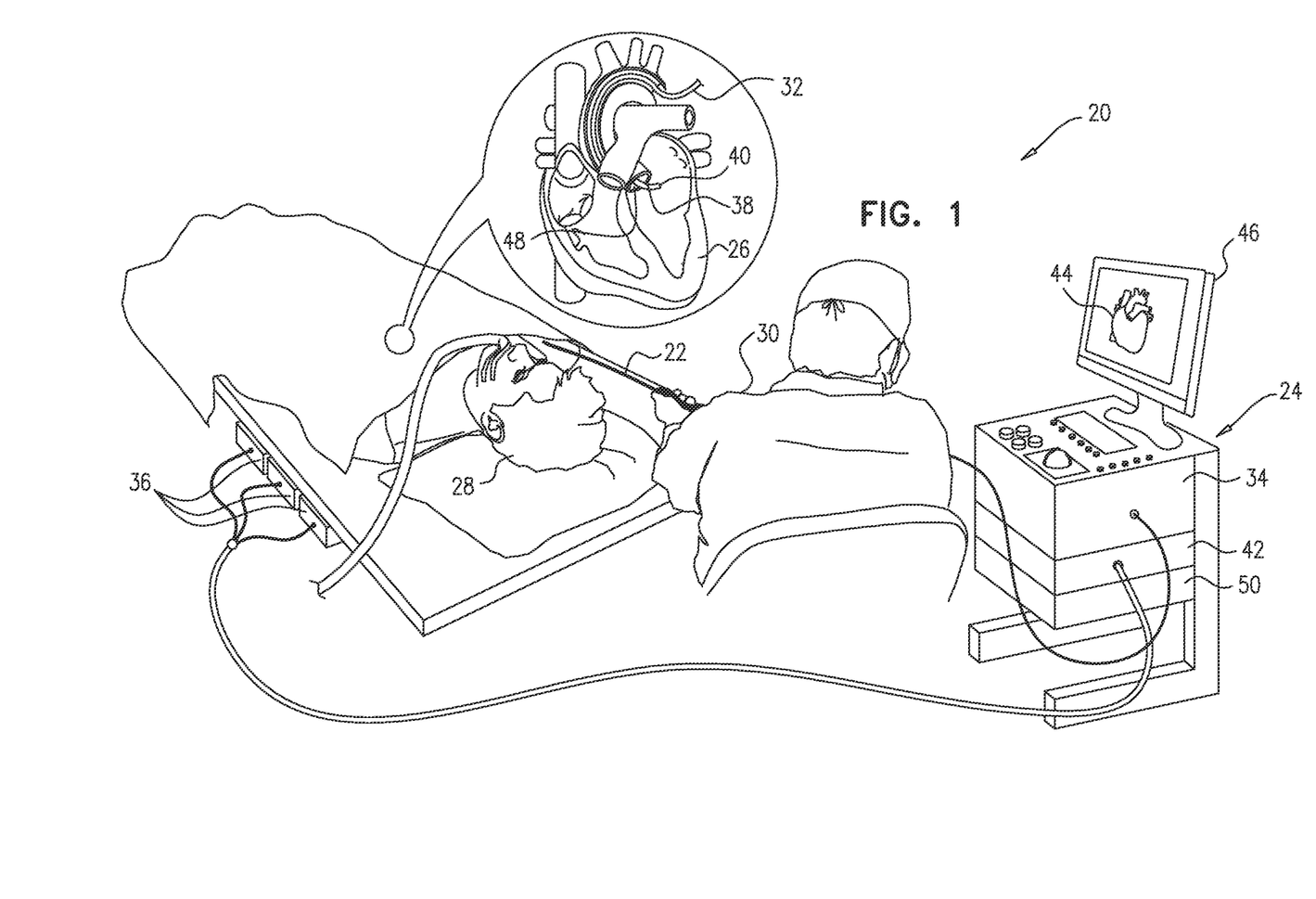
FIG. 1 is a schematic illustration of a system for ablation that carries out perforation risk estimation, in accordance with an embodiment of the present invention.

FIG. 1 is a schematic illustration of a system 20 for estimating the risk of tissue perforation during application of a minimally invasive procedure, in accordance with an embodiment of the present invention. System 20 comprises a probe 22, herein assumed to be a catheter, and a control console 24. In the embodiment described herein, it is assumed by way of example that probe 22 may be used for ablation of tissue in a heart 26 of a patient 28 in order to treat cardiac arrhythmias. Alternatively or additionally, probe 22 may be used for other therapeutic and/or diagnostic purposes, such as for mapping electrical potentials in the heart or in another body organ.

Console 24 comprises a processor 42, typically a general-purpose computer, with suitable front end and interface circuits for receiving signals from probe 22 and for controlling the other components of system 20 described herein. Processor 42 may be programmed in software to carry out the functions that are used by the system, and the processor stores data for the software in a memory 50. The software may be downloaded to console 24 in electronic form, over a network, for example, or it may be provided on non-transitory tangible media, such as optical, magnetic or electronic memory media. Alternatively, some or all of the functions of processor 42 may be carried out by dedicated or programmable digital hardware components.

An operator 30 inserts probe 22 through the vascular system of patient 28 so that a distal end 32 (also in FIG. 2 below) of probe 22 enters a chamber of heart 26. System 20 typically uses magnetic position sensing to determine position coordinates of the distal end inside heart 26. In this case console 24 comprises a driver circuit 34, which drives magnetic field generators 36 placed at known positions external to patient 28, e.g., below the patient's torso.

A magnetic field sensor 38 (also in FIG. 2 below) within the distal end of the probe generates electrical position signals in response to the magnetic fields from the coils, thereby enabling processor 42 to determine the position, i.e., the location and typically also the orientation, of distal end 32 within the chamber. The magnetic field sensor, (i.e., the position sensor) typically comprises one or more coils, usually three coils orthogonal to each other.

This method of position sensing is implemented, for example, in the CARTO™ system, produced by Biosense Webster Inc. (Diamond Bar, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

In an alternative embodiment, the roles of position sensor 38 and magnetic field generators 36 may be reversed. In other words, driver circuit 34 may drive a magnetic field generator in distal end 32 to generate one or more magnetic fields. The coils in generator 36 may be configured to sense the fields and generate signals indicative of the amplitudes of the components of these magnetic fields. Processor 42 receives and processes these signals in order to determine the position of distal end 32 within heart 26.

Although in the present example system 20 is assumed to measure the position of distal end 32 using magnetic-based sensors, embodiments of the present invention may use other position tracking techniques, for example, tracking systems based on impedance measurements. Impedance-based position tracking techniques are described, for example, in U.S. Pat. Nos. 5,983,126, 6,456,864 and 5,944,022, whose disclosures are also incorporated herein by reference. Other position tracking techniques, known to one having ordinary skill in the art, may be used to determine the position of the distal end 32. Thus, in the present application, the term position or displacement sensor is used to refer to any element which provides signals, according to the location and orientation of a probe or a section of a probe, such as the probe's distal end, to console 24.

The distal end of probe 22 also comprises a force sensor 48 (also in FIG. 2 below) which is able to provide electrical force signals to processor 42 in order to measure the magnitude and direction of the force on the distal end (or equivalently the force the catheter applies upon the tissue). The direction of the force is typically measured relative to the symmetry axis of the distal end. Various techniques may be used in measuring the force. Components and methods that may be used for this purpose are described, for example, in U.S. Patent Application Publications 2009/0093806 and 2009/0138007, whose disclosures are incorporated herein by reference and which are assigned to the assignee of the present patent application.

In order to ablate the tissue of heart 26, operator 30 manipulates probe 22 so that distal end 32 is at multiple locations on (or in close proximity to) the inner surface of the chamber. At each location, an electrode 40 coupled to the distal end measures a certain physiological property (e.g., the local surface electrical potential). Processor 42 correlates the location measurements, derived from the position signals of sensor 38, and the electrical potential measurements. Thus, the system collects multiple map points, with each map point comprising a coordinate on the inner chamber surface and a respective physiological property measurement at this coordinate.

Processor 42 uses the coordinates of the map points to construct a simulated surface of the cardiac chamber in question. Processor 42 then combines the electrical potential measurements of the map points with the simulated surface to produce a map of the potentials overlaid on the simulated surface. Processor 42 displays an image 44 of the map to operator 30 on a display 46.

In the embodiments described herein, processor 42 uses at least the force and displacement measurements performed by sensors 38 and 48 to assess the risk of tissue perforation. Processor 42 presents audiovisual indications and alerts regarding the estimated risk on display 46, to enable operator 30 to take suitable measures, in advance, to prevent tissue perforation.

Figure 2:
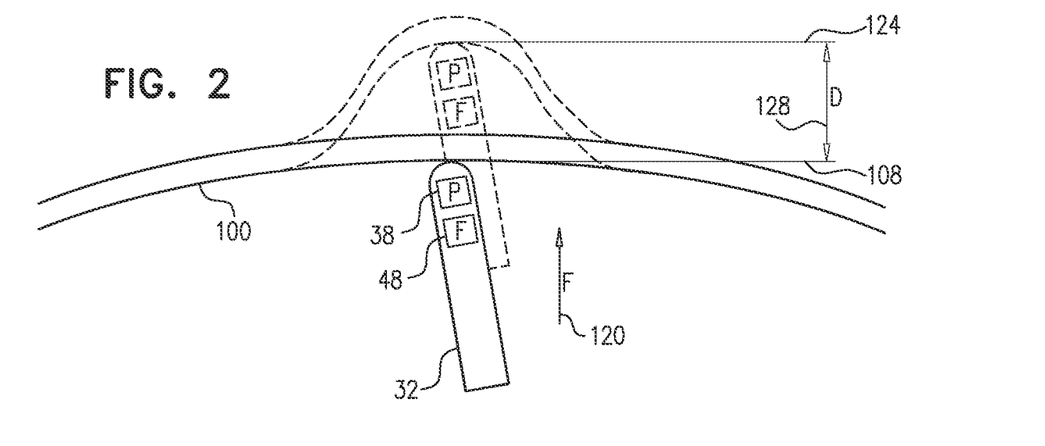
FIG. 2 is a schematic illustration of a probe performing cardiac ablation, in accordance with an embodiment of the present invention.

FIG. 2 is a schematic illustration of a probe causing tissue tenting, in accordance with an embodiment of the present invention. The figure depicts distal end 32 of a probe that is in contact with tissue surface 100. By way of example, tissue surface 100 may represent the inner surface of a chamber wall in heart 26. The probe comprises position sensor 38 and force sensor 48 as described above with reference to FIG. 1.

In order to apply ablation, operator 30 typically forces the probe towards the tissue. Note that the probe may be positioned perpendicularly to the tissue, or obliquely as depicted in the figure. As a result of a perpendicular force component F 120, the tissue is pushed in the force direction into a tenting position depicted in FIG. 2 in dashed lines. The position of the probe when it first comes into contact with the tissue is marked by a line 108 and in the tenting position by a line 124.

In an embodiment, position 108 serves as an initial or calibrated position for displacement measurements. The displacement between initial position 108 and position 124 is denoted D 128. Displacement D 128 is aligned with the direction of force F 120. Force sensor 48 and position sensor 38 are configured to measure F and D, respectively. Alternatively, processor 42 may use raw (i.e., non-calibrated) position and force magnitude/direction measurements to calculate D and F.

Various methods for measuring probe force and displacement are known in the art, and any such method can be used to measure F and D. For example, U.S. Patent Application Publication 2012/0310116, whose disclosure is incorporated herein by reference, describes a method that includes measuring a force exerted by a probe on tissue of a patient and measuring a displacement of the probe while measuring the force. The method further includes detecting a tenting of the tissue responsively to a relation between the measured force and the measured displacement.

As another example, U.S. patent application Ser. No. 13/680,496, filed Nov. 19, 2012, whose disclosure is incorporated herein by reference, describes a method that includes pressing a distal end of a medical probe against a wall of a body cavity, and receiving from the probe first measurements of a force exerted by the distal end on the wall. The method also includes receiving from the probe second measurements indicating a displacement of the wall in response to the force. The method further includes estimating a thickness of the wall based on the first and the second measurements.

Figure 3:
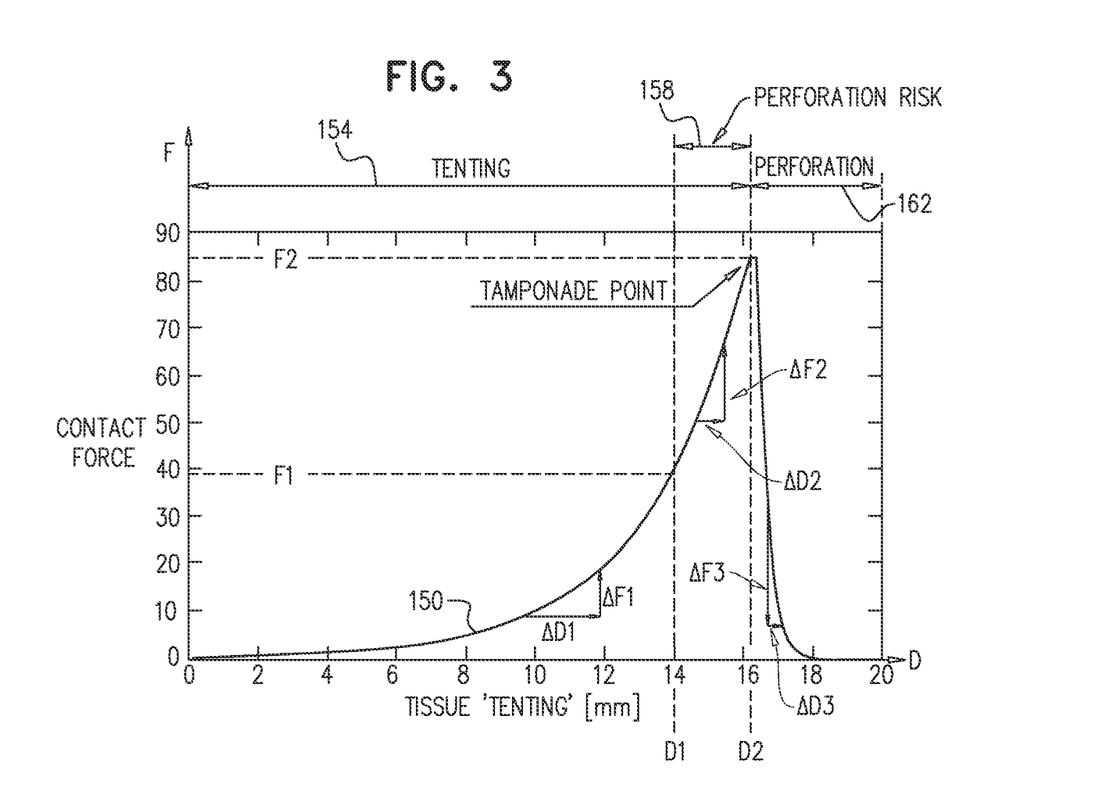
FIG. 3 is a graph showing a relationship between force and displacement of an invasive probe, in accordance with an embodiment of the present invention.

FIG. 3 is a graph 150 showing a relationship between force and displacement of an invasive probe, in accordance with an embodiment of the present invention. Graph 150 was created using a software simulation based on physical analysis and field experience of the inventors. The vertical force axis F and the horizontal displacement axis D may represent, for example, F 120 and D 128 of FIG. 2. Relationship 150 is depicted as a curve that is divided into three zones. In the range 0-D2, also referred to as a tenting zone 154, the flexibility of the tissue is maintained and the relationship between the force exerted upon the tissue and the respective displacement indicates a positive force-displacement gradient. In the tenting zone, F and D exhibit an increasing gradient behavior wherein the ratio between respective small changes in the force and displacement (i.e., the gradient or slope) $\Delta F1/\Delta D1$ at low force and displacement levels is smaller than the ratio $\Delta F2/\Delta D2$, which is measured at higher force and displacement levels.

In a perforation-risk zone 158, which resides at the upper end of tenting zone 154, the gradient of curve 150 at points of displacements in the range D1-D2 created by forces in the range F1-F2 is positive. The gradient $\Delta F2/\Delta D2$, however, in the perforation-risk zone, is significantly higher than in the 0-D1 zone. The behavior in zone 158 demonstrates that the tissue resistance significantly increases due to forces higher than F1, and therefore a larger force increase is required at the perforation-risk zone than in the 0-D1 zone in order to create similar displacement increases.

Perforation zone 162 relates to forces lower than F2 and displacements higher than D2 respectively. At the perforation zone the probe actually punctures the tissue and since the tissue no longer resists the force applied by the probe, force measurements drop rapidly and displacement measurements simultaneously increase. Note that in perforation zone 162 the curve gradient $\Delta F3/\Delta D3$ would be negative.

Figure 4:
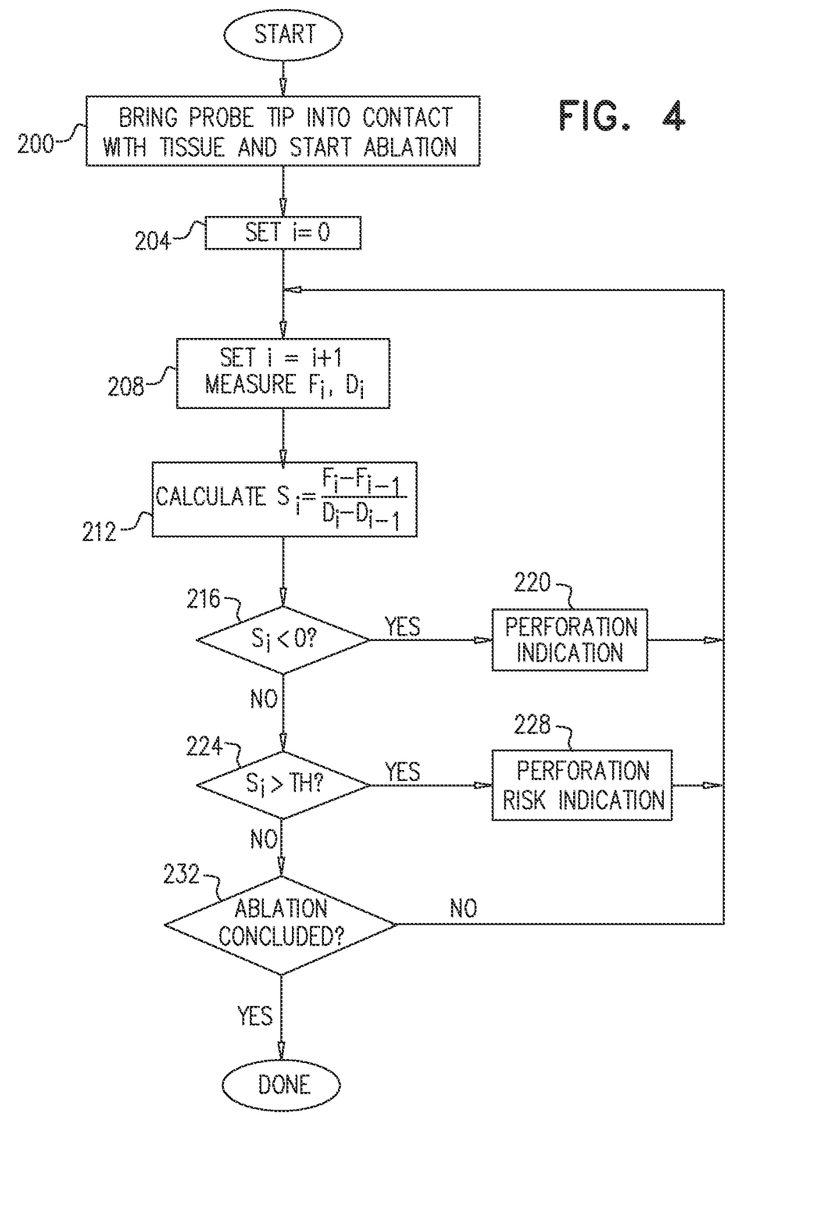
FIG. 4 is a flow chart that schematically illustrates a method for estimating the risk of tissue perforation, in accordance with an embodiment of the present invention.

FIG. 4 is a flow chart that schematically illustrates a method for estimating the risk of tissue perforation, in accordance with an embodiment of the present invention. Although the method is described with relation to cardiac ablation, the method is also applicable to non-ablation procedures as explained below. The method is additionally applicable to body organs other than the heart. The method begins by operator 30 inserting the catheter into heart 26 and bringing distal end 32 in contact with the tissue at the site for ablation (or possibly other probe-based treatment) at an initiation step 200. At this point, force and position sensors 48 and 38 start performing respective measurements that are delivered to processor 42. Processor 42 resets a measurement index i at an index reset step 204.

Processor 42 gets a force and displacement measurement pair $F_i$ and $D_i$ at a measuring step 208. Processor 42 increments index i and saves $F_i$ and $D_i$ in memory 50. Upon receiving new measurements, processor 42 calculates an instantaneous slope or gradient value $S_i$ at a gradient calculation step 212. Processor 42 calculates a force change $\Delta F_i = F_i - F_{i-1}$ and a displacement change $\Delta D_i = D_i - D_{i-1}$ relative to the previous measurement index i−1. The processor calculates the instantaneous gradient $S_i = \Delta F_i/\Delta D_i$ and saves $S_i$ in memory 50. Note that if either $|\Delta F_i|$ or $|\Delta D_i|$ is below a predefined threshold (e.g., $|\Delta D_i|$ is close or equal to zero), the instantaneous gradient result may be unreliable. In such cases the calculation of $S_i$ at step 212 is skipped and $S_i$ may be discarded or copied from $S_{i-1}$. In some embodiments, processor 42 uses smoothed measurements by averaging a predefined number of successive $\Delta F_i$ and $\Delta D_i$ samples. Note that averaging the difference samples $\Delta F_i$ between the indices i and i+M, is equivalent to taking the difference $\Delta F_{i+M} - \Delta F_{i-1}$ (a similar argument holds for the displacement differences). In yet alternative embodiments processor 42 averages the instantaneous gradient values $S_i$.

Processor 42 then checks the sign of the gradient at a sign checking step 216. If $S_i < 0$ perforation has presumably occurred and processor 42 indicates a perforation alert to operator 30 at a perforation indication step 220. Otherwise, processor 42 checks whether the current gradient $S_i$ is greater than a threshold TH at a slope comparison step 224. If $S_i >$TH, the force and displacement are assumed in the perforation-risk zone, and processor 42 alerts a perforation-risk indication at a perforation-risk indication step 228. The method proceeds to check if the ablation is concluded at a termination check step 232.

Various methods can be used to detect conclusion of the probe-based medical procedure. For example, operator 30 may decide that the medical procedure is completed for the current site by examining respective indications on display 46. Alternatively or additionally, processor 42 can be configured to automatically decide if the medical procedure is completed. In embodiments in which probe 22 and processor 42 share a communication channel (e.g., as in the CARTO system), operator 30 can signal to processor via this communication channel of start and/or end events regarding the medical procedure.

If at step 232 the ablation is not concluded the method loops back to step 208 to collect subsequent measurements. Otherwise, ablation is concluded and the method terminates.

The indications alerted to the physician at steps 220 and 228 above are typically presented on display 46. For example, the processor may preset a possibly blinking warning text. Alternatively or additionally, the processor may activate a suitable audible sound to alert the operator. Further alternatively or additionally, the processor may activate any other suitable indication to alert the operator of a perforation or perforation-risk situation.

Typically, the warning alert at step 220 would be different and more noticeable than the alert indicated at step 228. The operator should respond to a perforation alert by taking immediate suitable measures to treat the medical situation as known in the art.

Upon receiving a perforation-risk indication, operator 30 may take any suitable action to prevent tissue perforation. For example, the operator can pull back the probe to reduce the force applied to the tissue. Alternatively or additionally, the operator may reduce or even shut down the RF energy applied to the tissue (e.g., in ablation). Further alternatively, the operator can proceed to perform ablation at another tissue site, and resume ablating the current site at a later occasion. In alternative embodiments, processor 42 automatically reduces or shuts down the RF energy upon entering the perforation and/or perforation-risk zones.

The method described in FIG. 4 is an exemplary method, and other suitable methods can also be used. For example, in addition to using the gradient value to estimate the perforation-risk level at step 224, force and displacement values may also be considered, wherein higher values indicate higher risk of perforation. As another example, processor 42 may use smoothed force and displacement measurements by applying a moving average window or any other smoothing method over multiple Si values at step 212.

In some embodiments, the method of FIG. 4 is used for probe-based medical procedures other than ablation and possibly in body organs other than the heart. In such procedures, applying a probe force upon the organ tissue can still result in perforation to the organ tissue. Since, however, ablation typically weakens the tissue, when ablation is applied the instantaneous gradient values are expected to be lower, and therefore the gradient threshold for detecting perforation or perforation-risk should be configured to a lower value relative to non-ablation procedures.

Although the embodiments described herein mainly address estimating the risk of perforating the heart tissue during ablation, the methods and systems described herein can also be used in other applications, such as in performing any medical procedure in which a probe may apply excessive force upon the tissue of an organ of the body.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method for performing a medical procedure, comprising:
providing an electrode proximal to a distal end of the probe;
providing a magnetic field sensor within the distal end of the probe, the magnetic field sensor configured to generate electrical position signals; and
providing a processor, which is coupled to the probe and is configured to
measure a mechanical force exerted by the tip on the tissue and a displacement of the tip created by the force,
to calculate a dependence of the mechanical force on the displacement, and
to estimate, based on the calculated dependence, a risk level of perforation of the tissue due to the mechanical force of the probe tip on the tissue,
coupling the probe tip to tissue in an organ of a patient in order to apply the medical procedure using the probe;
measuring a mechanical force exerted by the tip on the tissue and a displacement of the tip created by the force;
calculating a dependence of the mechanical force on the displacement; and
estimating, based on the calculated dependence, a risk level of perforation of the tissue due to the mechanical pressure of the probe tip,
wherein the electrode is configured to measure local electrical potential at a plurality of locations in the organ of the patient to obtain a plurality of local electrical potential measurements,
wherein the processor is configured to correlate the location measurements, derived from the electrical position signals of the magnetic field sensor, with the local electrical potential measurements to determine a plurality of map points,
wherein each of the map points comprises a coordinate on an inner surface of the organ and a respective local electrical potential measurement at the coordinate,
wherein the processor is adapted to employ the coordinates of the map points to construct a simulation of the inner surface of the organ, and
wherein the processor is adapted to combine the local electrical potential measurements of the map points with the simulation of the inner surface of the organ to produce a map of electrical potentials overlaid on the simulation of the inner surface of the organ,
wherein the processor is configured to perform the steps of:
setting a measurement index,
receiving a first force measurement and first displacement measurement pair,
incrementing the measurement index and saving the first force measurement and first displacement measurement in a memory,
upon receiving a second force measurement and second displacement measurement pair, calculating an instantaneous gradient value ($S_i$), based on the change in force ($\Delta F_i$,) and a change in displacement ($\Delta D_i$,), and saving the instantaneous gradient value ($S_i$) in the memory, wherein when either the change in force ($\Delta F_i$,) or the change in displacement, ($\Delta D_i$,) are below a predefined threshold, a previously-calculated instantaneous gradient value ($S_i$) is saved in the memory, and
checking the instantaneous gradient value ($S_i$), wherein when the instantaneous gradient value ($S_i$) is negative, issuing an alert that perforation has occurred and when the instantaneous gradient value ($S_i$) is not negative, proceeding to a slope comparison step, the slope comparison step comprising the step of determining whether the instantaneous gradient value ($S_i$) is greater than a gradient value threshold (TH), wherein when the instantaneous gradient value ($S_i$) is greater than a gradient value threshold (TH), the processor issues an alert indicating a perforation risk,
wherein the processor automatically issues instructions to reduce a supply of RF energy to the probe when the instantaneous gradient value ($S_i$) is negative, and
wherein the processor automatically issues instructions to reduce the supply of RF energy to the probe when the instantaneous gradient value ($S_i$) is greater than a gradient value threshold (TH).

2. The method according to claim 1, wherein calculating the dependence comprises calculating a gradient of the force as a function of the displacement, and wherein estimating the risk level comprises comparing the gradient to a predefined gradient threshold.

3. The method according to claim 2, wherein estimating the risk level comprises predicting that the perforation is not imminent upon detecting that the gradient is lower than the predefined gradient threshold.

4. The method according to claim 2, wherein estimating the risk level comprises predicting that the perforation is imminent upon detecting that the gradient is higher than the predefined gradient threshold.

5. The method according to claim 1, wherein estimating the risk level comprises identifying that the perforation has occurred upon detecting that the force is inversely-related to the displacement.

6. The method according to claim 1, wherein measuring the displacement comprises measuring a first position when the tip is initially coupled to the tissue, measuring a second position when the tip exerts the force on the tissue, and calculating the displacement as the difference between the second and the first positions.

7. The method according to claim 1, and comprising indicating the estimated risk level to an operator of the medical procedure.

8. The method according to claim 7, wherein indicating the risk level comprises indicating an audible or visual alert.

9. The method according to claim 7, wherein indicating the risk level comprises outputting a first indication if the risk level indicates an imminent perforation, and outputting a second indication, different from the first indication, if the risk level indicates an actual perforation.

10. A method for performing a medical procedure, comprising:
providing a processor, and a probe operatively linked to the processor;
coupling a tip of the probe to a tissue in an organ;
measuring a mechanical force exerted by the tip on the tissue, and measuring a displacement of the tip created by the mechanical force,
calculating a dependence of the force on the displacement, and
estimating, based on the calculated dependence, a risk level of perforation of the tissue due to the mechanical force of the probe tip against the tissue,
wherein the step of estimating a risk level of perforation comprises:
setting a measurement index,
receiving a first force measurement and first displacement measurement pair,
incrementing the measurement index and saving the first force measurement and first displacement measurement in a memory, checking the instantaneous gradient value ($S_i$), upon receiving a second force measurement and second displacement measurement pair, calculating an instantaneous gradient value ($S_i$), based on the change in force ($\Delta F_i$) and a change in displacement ($\Delta D_i$) and saving the instantaneous gradient value ($S_i$) in the memory, wherein when either the change in force ($\Delta Fi$,) or the change in displacement, ($\Delta D_i$,) are below a predefined threshold, a previously-calculated instantaneous gradient value ($S_i$) is saved in the memory, and checking the instantaneous gradient value ($S_i$),
when the instantaneous gradient value ($S_i$) is negative, issuing an alert that perforation has occurred and
when the instantaneous gradient value ($S_i$) is not negative, proceeding to a slope comparison step,
the slope comparison step comprising determining whether the instantaneous gradient value ($S_i$) is greater than a gradient value threshold (TH), and in response to the instantaneous gradient value ($S_i$) being greater than a gradient value threshold (TH), issuing an alert indicating a perforation risk.

11. The method of claim 10, further comprising the processor automatically issuing instructions to reduce a supply of RF energy to the probe when the instantaneous gradient value ($S_i$) is negative.

12. The method of claim 10, further comprising the processor automatically issuing instructions to reduce the supply of RF energy to the probe when the instantaneous gradient value ($S_i$) is greater than a gradient value threshold (TH).

13. The method of claim 10:
wherein the organ is a heart;
wherein the probe comprises an electrode configured to measure electrical potentials;
measuring electrical potentials at a plurality of locations in the heart of the patient to obtain a plurality of local electrical potential measurements, and determining corresponding coordinates of said plurality of locations in the heart; and
determining and displaying a map of said plurality of local electrical potential measurements at the corresponding coordinates of said plurality of locations in the heart.

14. The method of claim 10:
wherein the probe comprises an electrode configured to measure local electrical potentials, and a magnetic field sensor configured to generate electrical position signals;
using the electrode, measuring local electrical potential at a plurality of locations in the organ of the patient to obtain a plurality of local electrical potential measurements;
correlating a plurality of location measurements, derived from the electrical position signals of the magnetic field sensor, with said local electrical potential measurements to determine a plurality of map points;
wherein each of the map points comprises a coordinate on an inner surface of the organ and a respective local electrical potential measurement at the coordinate;
constructing a simulation of the inner surface of the organ using the coordinates of the map points; and
combining the local electrical potential measurements of the map points with the simulation of the inner surface of the organ to produce a map of electrical potentials overlaid on the simulation of the inner surface of the organ, and displaying the map of electrical potentials overlaid on the simulation of the inner surface of the organ.

15. The method of claim 14, further comprising indicating a risk level to an operator of the medical procedure using at least one of an audible alert and a visual alert.

16. The method of claim 14, further comprising:
indicating a first risk level to the operator which indicates imminent perforation, and
indicating a second risk level to the operator which indicates perforation has occurred;
wherein the first risk level and the second risk level are indicated to the operator using different alerts.

17. The method of claim 10, further comprising indicating a risk level to an operator of the medical procedure using at least one of an audible alert and a visual alert.

18. The method of claim 10, further comprising:
indicating a first risk level to the operator which indicates imminent perforation, and
indicating a second risk level to the operator which indicates perforation has occurred;
wherein the first risk level and the second risk level are indicated to the operator using different alerts.

19. The method of claim 10:
wherein the organ is a heart;
wherein the probe is an ablation catheter;
the method further comprising ablating heart tissue.

* * * * *